United States Patent [19]

Gallegos et al.

[11] 4,006,227
[45] Feb. 1, 1977

[54] COMPOSITIONS AND METHODS FOR FERTILITY CONTROL

[76] Inventors: Alfred J. Gallegos, Calzada General Anaya 209; Vincente Cortés-Gallegos, Farallon 275, both of Mexico City, Mexico

[22] Filed: Nov. 4, 1974

[21] Appl. No.: 520,646

Related U.S. Application Data

[63] Continuation-in-part of Ser. No. 416,212, Nov. 15, 1973, abandoned.

[52] U.S. Cl. ............................................... 424/195
[51] Int. Cl.$^2$ ...................................... A61K 35/78
[58] Field of Search ................................... 424/195

[56] References Cited
OTHER PUBLICATIONS

Colin, J.A.P.A., vol. 18 (1929), pp. 876–880.

Martinez, Las Plantas Medicinales de Mexico (1944), pp. 331 to 338.

*Primary Examiner*—Sam Rosen
*Attorney, Agent, or Firm*—Sidney W. Millard

[57] ABSTRACT

A pharmaceutical composition obtainable by extraction from *Montanoa tomentosa* is useful for controlling fertility in female mammals. By internal administration of an effective luteolytic amount of the herbal product, blood levels of progesterone can be controlled and in the case of female humans and other primates such as monkeys, menses may be induced. Antiimplantation or pregnancy termination methods may be utilized for humans and lower animals. Biologically synchronized and controlled fertility techniques permit members of a mammalian group to become fertile in a close time period for reducing the time span in which newborn animals, such as sheep, are delivered.

17 Claims, 9 Drawing Figures

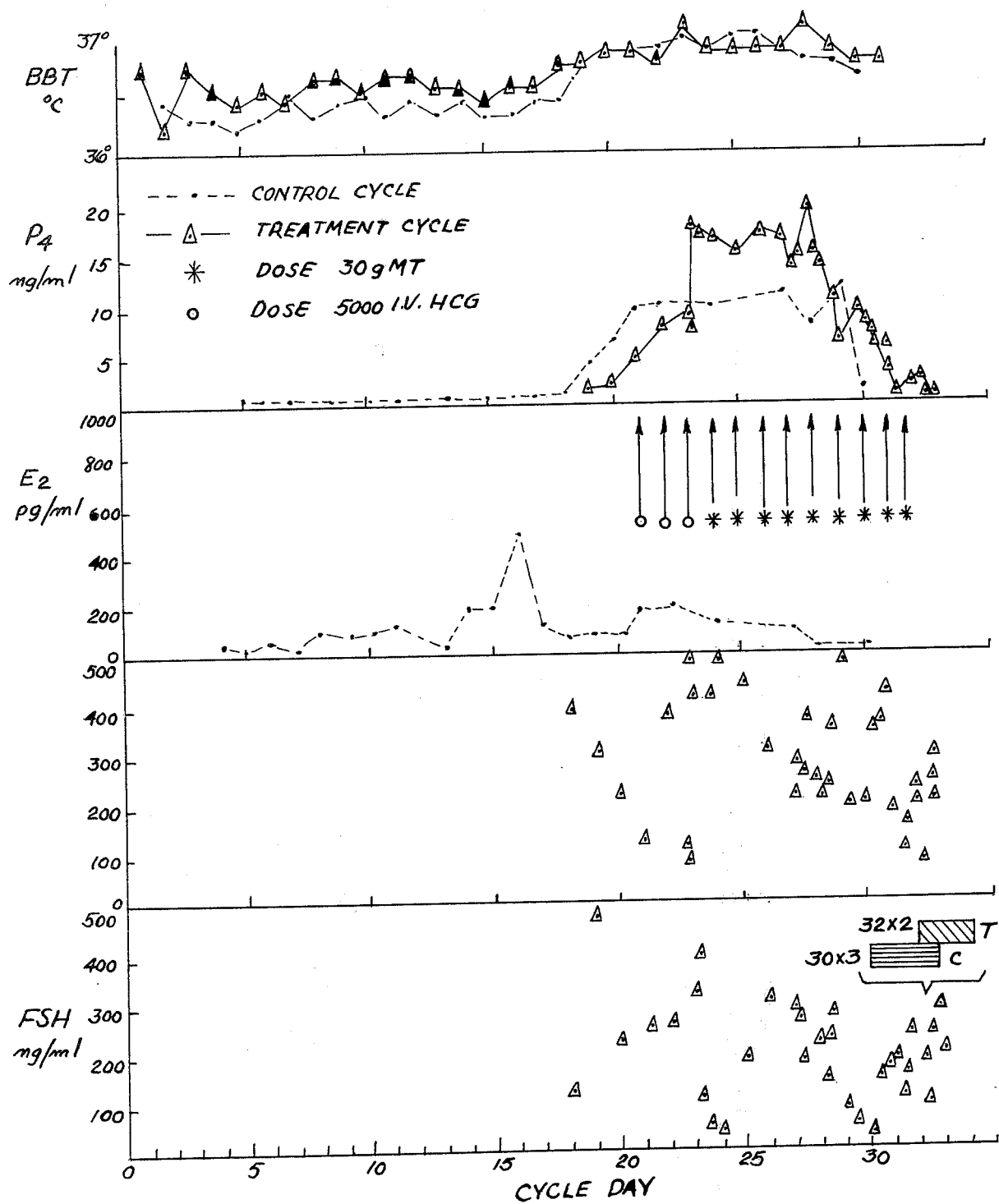

COMPOSITIONS AND METHODS FOR FERTILITY CONTROL

REFERENCE TO COPENDING APPLICATIONS

This application is a continuation-in-part of copending U.S. Pat. application Ser. No. 416,212, filed Nov. 15, 1973, now abandoned.

BACKGROUND OF THE INVENTION

This invention relates to fertility control in mammals. In particular, it provides novel, unit dosage, pharmaceutical compositions for reducing blood levels of progesterone.

Orally administered contraceptive medication is now widely practiced in humans, utilizing synthetic progestational and estrogenic substances to produce the same effects as the corresponding natural hormones.

At the beginning of the reporductive cycle in mammals, follicle stimulating hormone (FSH) and luteinizing hormone (LH) are secreted from the pituitary gland and stimulate growthn of the ovarian follicles containing the ova. As the follicles grow and develop, estrogen hormones (principally estradiol) are secreted from the follicles in increasing amounts. In the human cycle, high blood levels of estradiol, somewhere around day 12 – 16 of the cycle, stimulate a large secretion of LH which produces ovulation. At this point in time, the woman's basal body temperature (BBT) falls to its lowest point during the cycle. After ovulation (expulsion of ovum from ovary into oviduct), the follicle cavity undergoes cellular changes and is transformed into a body called a corpus luteum. This corpus luteum principally secretes another ovarian hormone, progesterone. This hormone, together with earlier stimulation by estrogen, prepares the lining of the uterus (endometrium) for acceptance of the fertilized ovum (implantation) if the woman has become pregnant. These same hormones "feed back" to inhibit FSH and LH secretion if the woman is pregnant, and no further ovulation occurs until pregnancy has been completed. This biological principle has been applied through use of oral contraceptives; "the pill" contains synthetic estrogens and progestational compounds which act to inhibit FSH and LH and prevent ovulation.

The known methods of ovulation control or prevention have usually involved the oral administration of combined progestational and estrogenic substances at some stage of the cycle. The earlier method, known as combined treatment, involved administering a combination of progestational and estrogenic substances usually on the 5th day after the beginning of the menstrual period, and prior to ovulation, for a period of about 21 days, followed by a cessation until the next cycle. An alternative method, the sequential treatment, only the estrogenic substance is administered for about 16 days, and then a combination dosage for about 5 or 6 days, followed by cessation until the resumption of the cycle.

The use of estrogens in ovulation control is regarded as questionable by some in the medical profession, because of side effects in a small percentage of woman.

There have been attempts to control fertility employing only progestational substances, without estrogens, in which the progestational agents were administered continuously throughout the cycle. This resulted in excessive bleeding and irregular menses and possibly some toxic effects due to continuous exposure.

Another way conception can be blocked is by inhibiting or reducing the secretion of progesterone from the corpus luteum after ovulation so that implantation will not occur or, in the event that it occurs, the endometrium cannot support development of the fertilized ovum.

Intensive research has been aimed toward the development of safe, self-administered methods and compositions for terminating human pregnancies during the first trimester. Prostaglandin and its analogues or other related compounds are known to induce menses and abortion; however, the proportion of complete first trimester abortions by this procedure is not sufficiently high to permit such treatment, except as an adjunct to suction currettage. Termination of second trimester pregnancies usually requires a more closely-supervised method to assure safety and effectiveness. Prior art methods include intra-uterine injection of hypertonic saline solution and intra-amniotic injection of prostaglandin. A study of chromosome breakage in peripheral lymphocytes of woman on oral contraceptives indicates a small but statistically significant increase in chromosomal breakage among oral contraceptive users. Chromosomal aberrations may increase among offspring of women who conceived while using oral contraceptive therapy.

Prostaglandin and similar compounds have potential utility as luteolytic agents (chemicals which reduce the function of the corpus luteum), uterine stimulants, or menses inducers for use as once-a-month pills. Natural and synthetic prostaglandins have been demonstrated to have luteolytic activity in other mammals but not in humans. However, the presently available prostaglandins have a number of side effects which impose a limitation on their utility in fertility regulation.

Progesterone is often referred to as the hormone of pregnancy because its action on the uterus is required for the maintenance of pregnancy in the human as well as in other mammalian species. There are very specific uterine responses to progesterone hormone stimulation in the mammal and the role of this steroid is becoming better understood with regard to fertility control.

When progesterone enters the cell, it is bound to the cytoplasmic receptor and subsequently to the nuclear receptor. Selective binding of progestational drugs to receptors in the uterus is now indicated. The biological properties of progesterone provide a similar role in most mammals in the reproductive system. Accordingly, the use of active compositions for controlling plasma progesterone with minimum side effects is an important goal of contraceptive research and development.

The use of naturally occurring materials for medicinal purposes has drawn attention to numerous plants as sources for pharmacologically active products. In the fields and mountains of Mexico grow several species of zoapatle. Various species of the zoapatle genus are reputed to have stomachic, diuretic and pectoral properties. Zoapatle species can also provide uterine contractions and can be used as an aid in childbirth by oral administration of an infusion of leaves. In "Contributions From the National Herbarium," Smithsonian Institution, Vol. 23, Part 5, pp. 1529–37 P. C. Standley describes the Montanoa genus among the trees and shrubs of Mexico. Various references cite the species *Montanoa tomentosa*, which may be taken orally by humans as a decoction of the leaves at the time of delivery to facilitate labor in childbirth and to prevent subsequent exhaustion. The naturally occurring starting product may be harvested at any time of the year, although the relative strength of active constituents may vary seasonally or with climatic or soil conditions.

SUMMARY OF THE INVENTION

It has been found that an active luteolytic constituent of a zoapatle plant native to Mexico can be extracted and administered internally to reduce progesterone levels in blood. This discovery can be employed in several useful ways to control fertility in mammals, including quadrupeds and primates. Compositions suitable for inducing menses in primates have been prepared from the active component of *Montanoa tomentosa* (MT), which substance is obtainable by boiling leaves, twigs, or stems of the plant in water to extract the active constituent. A standardized unit dosage is prepared as an aqueous decoction from about 15 to 30 grams of the plant per 200 cc of water (75 to 150 gMT/liter).

When the phrase "induce menses" is used herein it will be understood that reference is to primates, usually the human female. However, where the phrase "reduce blood levels of progesterone" is used it will be understood that reference is to all mammals, including primates.

The composition is useful to induce menses in humans and other primates. This object can be achieved by internally administering a luteolytic amount of the extract at a predetermined time in the menstrual cycle. Fertility control available according to the objects of this discovery may be employed for prevention or termination of pregnancy in mammals.

Accordingly, it is an object of the present invention to provide a new oral contraceptive in extract form. In particular, providing a composition equivalent to the herbal product extracted from the plant, *Montanoa tomentosa*, is an object, which is further implemented by particular methods for using the composition in an effective amount of the progesterone-regulating component. Another object is to reduce the blood levels of progesterone by oral administration of an herbal extract. It is a further object of this invention to provide a pharmaceutical composition to induce menses in mammals by progesterone control while having substantially no deleterious side effects. Yet another object is to provide menses-inducing materials in pharmaceutically acceptable form containing an improved active constituent obtainable by extraction from a Zoapatle species with water and heat. Other objects include methods for terminating pregnancy or regulating fertility in adult mammalian females by internal administration. Other objects include methods for delivering newborn animals from a group of female mammals at term or near term in a biologically synchronized time span by administering the herbal product or its synthetic chemical equivalent to control conception and permitting members of the group to become fertile in a close time period, that is, synchronizing the estrous cycle of cattle or other animals. Other objects and advantages of the invention will become apparent to the skilled reproductive biologist, physician, mammalogist or veterinarian in accordance with the following examples and information.

THE DRAWINGS

FIGS. 1–9 are graphic plots of human menstrual cycles showing basal body temperature and progesterone ($P_4$) levels in blood plasma for ten subjects during a control cycle and a treatment cycle. Blood levels of 17-$\beta$-estradiol ($E_2$), luteinizing hormone (LH) and follicle stimulating hormone (FSH) are shown for several of these subjects in FIGS. 4, 5, 6, 7, 8, and 9.

DESCRIPTION OF THE PREFERRED EMBODIMENTS

Figure 1:
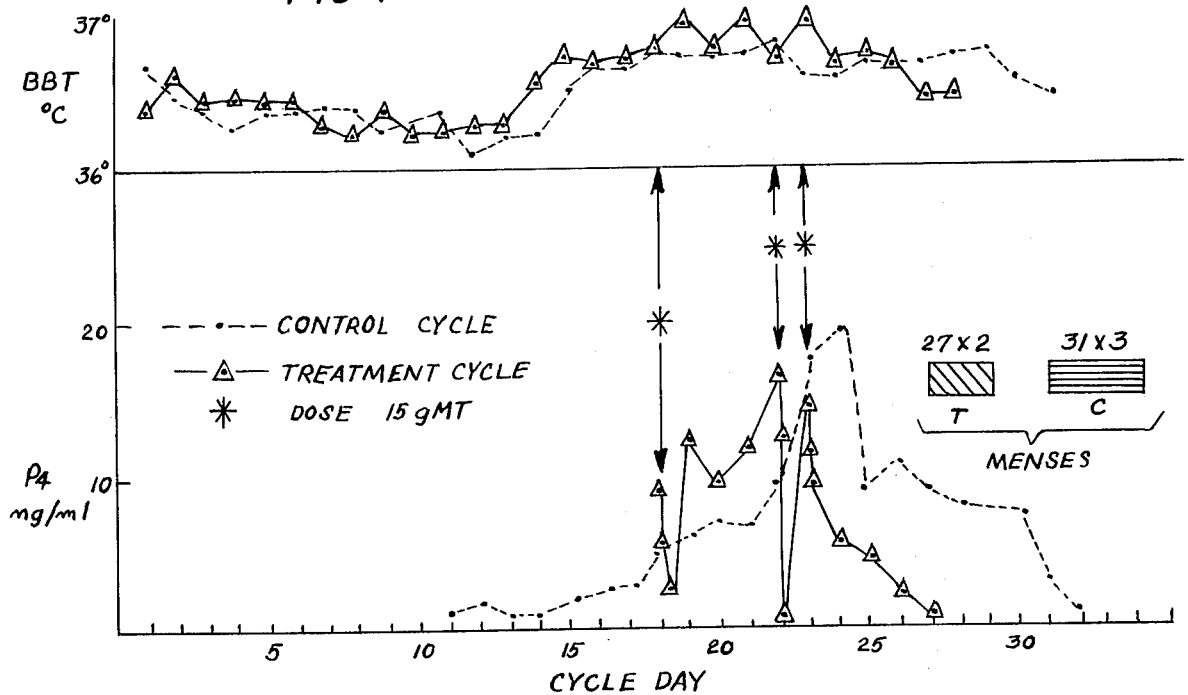

In the specification metric units and parts by weight are employed unless otherwise indicated. The standard manner of expressing the extract shall be understood as the weight (grams) of dry leaves of *Montanoa tomentosa* (MT) per volume of water (liters or ml.). The aqueous extract was investigated to determine electrolyte content by boiling 50 g of MT in 2 liters of water and dialyzing the extract overnight against deionized water, concentrated to obtain a final volume of 106 ml. By atomic absorption spectrometric the following was found:

Potassium, 0.8 mg/l; calcium, 290 mg/l, sodium, 14 mg/l; magnesium, 105 mg/l;

The active luteolytic component of *Montanoa tomentosa* may be extracted with weak aqueous solutions which do not contain materials deleterious to the active component; other solvents or mixtures are obvious equivalents. Aqueous infusion of zoapatle species is a preferred method for obtaining the active component as an orally administered tea or decoction prepared by hot leaching the leaves and/or stems with water. The separation process may employ solid-liquid contact in batch or semi-continuous extraction, for instance, counter-current multistage leaching. Considering the plentiful supply of zoapatle species, no particular advantage is found for elaborate recovery processes at the present time. The liquid extract phase containing the active component may be separated from the leached solids by centrifuging or filtering. The liquid phase may be concentrated by evaporating the solvent to obtain an active residue. Other separation procedures for recovering the active luteolytic component are within the skill of the art. Further purification by precipitation, dialysis, diffusion, or other mass transport methods are contemplated within the inventive concept. Aqueous extraction by boiling (at about 100° C.) for 15–20 minutes is the standard method for preparing decoctions herein unless otherwise specified.

A pharmaceutically acceptable composition in oral unit dosage form may be prepared as a liquid to be administered by drinking. Also, the active component in concentrated form may be administered orally as a dissolvable capsule, quick-dissolving tablet or in time release form as a once-per-period dosage. Various inert pharmaceutical ingredients or carriers may be employed, with the active substance, including lactose, glucose, sucrose, salts, cellulose, starches, kaolin, gelatin, polyvinylpyrrolidone, alkaline earth stearates, paraffins, trigylcenide oils, etc., to prepare the active substance for internal administration.

Any medically acceptable method of getting the active substance into the bloodstream will be effective to reduce plasma progesterone. For instance, it can be admixed with a low melting inert substance and administered internally as a daily suppository, either vaginally or rectally. Administration through the alimentary canal is most commonly used; however, parenteral methods are acceptable in many cases. The active constituent can pass through the wall of the gastrointestinal tract or the vaginal mucosa into the bloodstream where the luteolytic action can take place to reduce the blood levels of progesterone.

The active substance can be administered to mammals by mixing with food or other ways obvious to those having ordinary skill in the art. The shelf life under ordinary conditions permits packaging of predetermined unit dosage amounts for each mammalian species. The substance can be used in pet food to control their populations.

The active luteolytic component of *Montanoa tomentosa* may be employed to interrupt pregnancy in mammals in the early stages. Numerous medical and veterinary reasons for aborting the fetus exist in addition to population control for man and lower mammals. Toxemia, prenatal disease, cardiac conditions, mismating and undesired pregnancy are common reasons for terminating a pregnancy.

In certain veterinary practices, it is desirable to synchronize births in a group of mammals for economic purposes. Sheep flocks or other cattle herds can be subjected to biological synchronization to control the time span during which births occur if the females can be controlled in their fertility at the beginning of seasonal fertilization periods. Such synchronizing of the estrous cycle could produce more than a single offspring per female in a herd in a one year period, there could be two or more deliveries in a year in some species. Similarly, such biological synchronous control can result in great efficiencies for delivering an entire flock within a relatively short time span (i.e., days) rather than permit the flock births to occur naturally over a period of several weeks. Total time in attendance required for delivery of the offspring from a herd, flock, drove, pack, or other aggregation of animals can be reduced by controlling the time span for births in a group using a luteolytic composition to regulate the beginning of the pregnancies. Dosage amounts equivalent to about ¼ to 40 gMT/Kg of body weight are effective and non-toxic.

In order to demonstrate the biological properties of MT extract, experiments were made on albino Sprague-Dawley rats.

ANTI-IMPLANTATION EFFECTS

Example 1

A series of two studies was performed in order to ascertain the anti-fertility efficacy of oral administration of MT aqueous extract in the female rat. The extract was obtained by boiling 50 g. of dry MT plant in 1 liter of water for 20 minutes to a final volume of 510 ml. In the afternoon of pre-estrous, groups of three animals were caged overnight with a male of proven fertility. The diagnosis of pregnancy was ascertained by the presence of spermatoza in vagina and the presence of endocervical plug. Starting 24 hours afting mating, in the next 8 days, each animal received daily doses of 0.5 ml of this aqueous extract and they were sacrificed on day 9 by a blow on the head. Animals were closely monitored by daily examination of epithelial vagina elements and vaginal cells. Similar control groups of animals received daily 0.5 ml of tap water through a gastric catheter. In final macroscopic observations all the animals at the time of sacrifice were in excellent condition with regard to appearance, behavior, and body weight. The results of these studies are given in Table 1.

The total number of implants in control animals were 108 while in the treated rats, total number of implants were only 39 (63.9% inhibition). Moreover, gross macroscopic abnormalities were found in 16 of the treated implants, leaving a total of 23 normal implants (78.8% inhibition).

TABLE 1

Results of Daily Administration for 8 Days of MT Extract to Pregnant Rats

| No. | Control (No. Implants) Left Horn | Control (No. Implants) Right Horn | Decoction Age* | Treated (No. Implants) Left Horn | Treated (No. Implants) Right Horn | Macroscopic Abnormalities | |
|---|---|---|---|---|---|---|---|
| 1 | 7 | 5 | 8 | 0 | 0 | 0 | 0 |
| 2 | 6 | 6 | 8 | 0 | 0 | 0 | 0 |
| 3 | 4 | 8 | 9 | 0 | 0 | 0 | 0 |
| 4 | 7 | 5 | 11 | 0 | 0 | 0 | 0 |
| 5 | 8 | 7 | 11 | 3 | 4 | 3 | 3 |
| 6 | 4 | 7 | 13 | 0 | 6 | 0 | 0 |
| 7 | 6 | 4 | 13 | 6 | 4 | 3 | 3 |
| 8 | 5 | 7 | 15 | 3 | 0 | 2 | 0 |
| 9 | 6 | 6 | 15 | 6 | 7 | 0 | 2 |
|   | 53 | 55 |   | 18 | 21 | 8 | 8 |
| Subtotal | 108 (100%) | | | 39 (63.9%) | | 16 | |
| Total Normal Embryos 108 | | | | 23 (78.8%) inhibition | | | |

*Number of days elapsed from preparation to the end of experiment.

The age of the decoction increases the number of implants present in the treated group.

In treated animals 1, 2, and 3, abundant liquid was found in both uterine horns and the ovaries were found surrounded by abundant liquid in the form of cysts. In treated animal No. 4, liquid was only found in both uterine horns. Treated animal No. 5 had 3 abnormal implants in the medium part of the left horn with abnormal spacing and with wrong orientation. The same abnormality was found in the right horn in the first three implants located at the medium portion of the uterine horn. Only one implant was found normal. In treated animal No. 6 implants found in the right horn were of normal appearance. The left ovary of the same animal was found very hemorrhagic. In treated animal No. 7, three out of the six implants found in the left horn were located in the superior portion and they were found abnormally closed and with wrong segmentation. The other three seemed to be normal. The same abnormality was seen in three out of the four implants found in the right horn. In treated animal No. 8, two were found in the left horn in the superior-position with abnormal spacing and orientation. The other one appeared normal. In treated animal No. 9, two out of seven implants in the right uterine horn were found without normal segmentation and spacing and were located in the superior portion of the right horn.

The control group had an average of six normal implants in each horn. However, in the treated group, only 39 were found, 18 implants being found in the left uterine horn and 21 in the right one. Moreover, out of these 39 implants, 16 were found with abnormalities either in the segmentation process and/or the orientation of the product.

Example 2

The procedure of Example 1 was repeated, except the aqueous extract was allowed to be no more than four days old. Results are presented in Table 11. Again the control group had 108 normal implants compared to 17 all in one rat in the treated group (74.3% inhibition). Moreover, gross abnormalities were found in those 17 embryos, wherein wrong spacing and wrong orientation were found in all implants. The normal implantation process in these species with the aqueous extract administered orally is suppressed by the MT extract.

TABLE II

Results of Daily Administration for 8 Days of MT Extract to Pregnant Rats

| No. | Control (No. Implants) Left Horn | Control (No. Implants) Right Horn | Decoction Age (Days) | Treated (No. Implants) Left Horn | Treated (No. Implants) Right Horn | Macroscopic Abnormalities | |
|---|---|---|---|---|---|---|---|
| 1 | 7 | 5 | 1-4 | 9 | 8 | 9 | 8 |
| 2 | 6 | 6 | 1-4 | 0 | 0 | 0 | 0 |
| 3 | 4 | 8 | 1-4 | 0 | 0 | 0 | 0 |
| 4 | 7 | 5 | 1-4 | 0 | 0 | 0 | 0 |
| 5 | 8 | 7 | 1-4 | 0 | 0 | 0 | 0 |
| 6 | 4 | 7 | 1-4 | 0 | 0 | 0 | 0 |
| 7 | 6 | 4 | 1-4 | 0 | 0 | 0 | 0 |
| 8 | 5 | 7 | 1-4 | 0 | 0 | 0 | 0 |
| 9 | 6 | 6 | 1-4 | 0 | 0 | 0 | 0 |
| Subtotal | 53 | 55 | | 9 | 8 | 9 | 8 |
| | 108 (100%) | | | 17 (74.3%) inhibition | | 17 | |
| Total Normal Embryos | 108 | | | 0 (100%) | | | |

Toxicological Studies of Oral Administration of Aqueous MT Extract

Acute toxicological studies were carried out in Sprague-Dawley rats with aqueous MT extract administered by the oral route. For these studies a total of 50 rats were used with body weights ranging from 162 to 240 g.

Example 3

In this experiment a single oral administration of the substance was used in different dosage amounts. The experimental animals were observed during 7 days and at the end of this time they were sacrificed by a blow in the neck followed by anatomopathological studies. Six female rats were selected at random for this experiment, with body weights ranging from 162 to 181 g., average 172 g. They were divided into three groups, and the aqueous extract was given orally. Group No. 1 received one dose equivalent to 41 g. of fresh MT herb per Kg. of body weight; Group 2 received 20.5 g. of fresh herb per Kg.; and Group No. 3, 10.2 g. of fresh herb per Kg.

The substance was administered in a volume of 3 ml. through a gastric catheter. Two limiting factors were present in this experiment: (1) with the administration of more than 3 ml. by oral route vomiting was induced in these animals, (2) the highest plant concentration in this aqueous extract was 175 g. per 100 ml. of water, and (3) a higher concentration produces a viscous material which is difficult to administer by the oral route. In one rat from Group No. 1, sedation and decrease of the motor activity was present and 24 hours later the animal was found dead. The necropsy of this animal showed hemorrhage of the thymus, arachnoid congestion and subserosal hemorrhage from the stomach wall. The cause of death could not be precised. The remaining animals did not show abnormal signs or symptoms. After 7 days of survival they were sacrificed and no abnormalities were found in the macroand microscopical observations. Normal weight gain was recorded for the test period.

Example 4

For this study 24 rats were used with body weights ranging from 165 to 218 g., average 187 g., and they were divided into four groups. Single dose administrations were as follows:

Groups 1, 2, 3, and 4, an equivalent of 25, 12.50, 6.25, and 3.12 g. of fresh MT herb per Kg. of body weight, respectively. The oral administration of the active substance was given for five days. The rats were observed for two hours after the oral administration of the compound and 12 hours later the same type of observation was made for approximately one hour. Afterwards all experimental animals were carefully observed daily for at least one hour until they were sacrificed. The signs and symptoms presented by the experimental animals were carefully recorded. Normal body weights were recorded before and after the administration of the compound. Water and chow were given "ad libitum" and the animals were housed in a controlled atmosphere. All the anatomopathological studies were performed within two hours from the time of sacrifice and the animals appeared normal macro- and microscopically.

Motor activity decreased in Group No. 1 with duration of two hours. No abnormal tissues were found in any of the animals on examination and all of them survived for 7 days.

Example 5

This is an acute experiment with repeated daily doses during five days. For this study 20 treated rats divided into four groups were used. The control group received distilled water instead of the plant infusion and the four experimental groups received the following oral doses: Group 1, 12.5 g.; Group 2, 6.25 g.; Group 3, 3.12 g.; Group 4, 1.56 g. The control group received 0 g. of fresh herb per Kg. of body weight. The only abnormality observed was an increase of irritability in the four groups of treated animals, but it was also present in the control group. After five days of observation the animals were sacrificed and the necropsy study was normal.

Example 6

For these studies oral administration of the aqueous MT extract was given by the oral route to 50 rats of the Sprague-Dawley strain. The animals received a single oral dose of the compound through a catheter and the doses given to these animals were equivalent to 3.12, 6.25, 12.5, 10.2, 20.5, and 41 g. of fresh herb per Kg. of body weight. These doses of plant extract are not considered toxic although in the highest dosage rate some animals decreased in motor activity. One rat was found dead without precising the cause of the death. The higher doses given are far in excess of any anticipated dosage to humans on a g/Kg. basis. Seven days after the single administration of the extract the animals were sacrificed and a complete necropsy and macro- and microscopical studies were performed. The following organs were histologically studied: brain, cerebellum, pituitary, heart, thymus, thyroid, liver, spleen, pancreas, kidney, lungs, adrenals, ovaries, uterus and fallopian tubes. No alterations were found.

Based on the above experimental data, it can be concluded that oral administration of *Montanoa tomentosa* has no toxic effects.

In the anti-implantation technique for controlling fertility, it is not clear whether the biological mechanism involves luteolytic or uterotonic properties of zoapatle. Nor is it known whether these separate properties are attributable to a single active component of the aqueous extract. Also, no present correlation for progesterone in primates can be made between potency of dry or wet weight basis for zoapatle plant leaves.

In order to demonstrate the uterotonic properties, relative potencies of uterine strip contractions were ascertained for a number of mammals. Zoapatle extract was compared to a standard oxytocin uterotonic solution, using in vitro bioassay procedures to estimate biological potency of the aqueous herbal extract. Tests were conducted on cat, guinea pig, hamster, rat, and *Macacus rhesus* (given in order of the observed sensitivity). Rat and Rhesus strips did not respond to Mt extract. Animals were sacrificed and the uteri were immediately excised. Uterine strips were placed in a chamber with tris buffer solutions at 37.5° C and bubbled with a mixture of 98% oxygen and 2% $CO_2$. Uterine contractility was recorded by using a transductor and a Grass 7B polygraph recorder. Zoapatle aqueous extract was obtained by boiling 50 g. of dry MT leaves in 2 liters of water and dialyzing against deionized water overnight to final volume of 106 ml. to remove excess electrolytes. In the standard tests, 0.2 to 1 ml. of the above MT extract was mixed with 5 ml. of buffered single-Krebs solution. The uterine contractility was measured during an initial control period during which the strip was contracting spontaneously and then the same strip with different amounts of MT extract. In the comparative tests, 1 ml. of MT extract was found equivalent to 0.242 mu of oxytocin for uterine contractility in cats.

The desired biological properties of MT extract are similar to prostaglandins (PGS); however, fewer side effects are observed. The uterotonic and luteolytic properties are present, as in PGS; however, the undesirable nausea, hypertension and increased irritability do not accompany MT treatment.

The MT extract has been found to reduce blood levels of progesterone ($P_4$) in humans and other primates. Nine human females were studied to determine the effects of MT on their significant reproductive characteristics. They were monitored for at least six months previous to this study and several parameters were observed. Length and characteristics of their menstrual cycles, daily charts of basal body temperature and plasma levels of progesterone were established for the control one month previous to treatment with MT. Each subject had bilateral tubal occlusion but was normally menstruating with a regular ovulatory pattern.

The MT extract was administered orally using a decoction of 15 g. or 30 gMT obtained by boiling the MT leaves in 200 ml water for 20 minutes.

Subjects 1-9 are correlated with FIGS. 1-9 of the drawing, respectively. Pertinent data appear below:

In FIG. 1 the control cycle (one previous to treatment) shows a normal BBT chart and progesterone ($P_4$) level. The zoapatle treatment was administered orally by drinking 15 gMT decoctions on the 18th, 22nd and 23rd day of the treated cycle. Following the third dose the temperature dropped within 24 hours. It is well documented that progesterone per se has no thermogenic effect. However, some of the metabolites of progesterone (5 β-reduced compound) exhibit thermogenic properties. The BBT temperature reduction is correlated with the significant reduction of progesterone levels. The menstrual cycle was shortened by 4 days. It was observed that with the administration of the second and third doses there were some minor abdominal cramps on the 22nd, 23rd, and 24th days. But more importantly, there were no changes in any of the vital functions, namely, cardiovascular, gastrointestinal, renal and respiratory systems. The reduction of progesterone levels resulting from the first oral administration of MT is on the 18th day as shown in FIG. 1. Immediately before treatment a blood sample was taken and the plasma level of progesterone was 9 ng/ml (nanograms per milliliter). After the MT extract was administered the blood level of progesterone dropped to 2.6 ng/ml in three hours. On the 19th day, the progesterone level had returned to the expected normal level and continued so for the two following days. On the 22nd day the second dose was administered immediately after the blood sample was taken before administration and the plasma levels of progesterone was 16.3 ng/ml. The progesterone level dropped to 0.5 ng/ml within 3 hours. On the 23rd day the progesterone level had been regenerated to 14.5 ng/ml. After the third MT extract dose was administered, within 3 hours thereafter the progesterone level came down only to 9.3 ng/ml. This initiated a steadily continuous decline until the 27th day when menses was initiated. The menses for the treatment cycle was initiated on the day 27 and continued for 2 days (T=27×2); whereas in the control cycle the menses began on day 31 and continued for 3 days (C=31×3).

It will be appreciated that a standard procedure for measuring the blood level of progesterone is to draw blood, separate the plasma and measure the progesterone levels in the plasma. Thus, the reference above and following is to blood plasma levels of progesterone because that was the measured characteristic.

Subject No. 2

Figure 2:
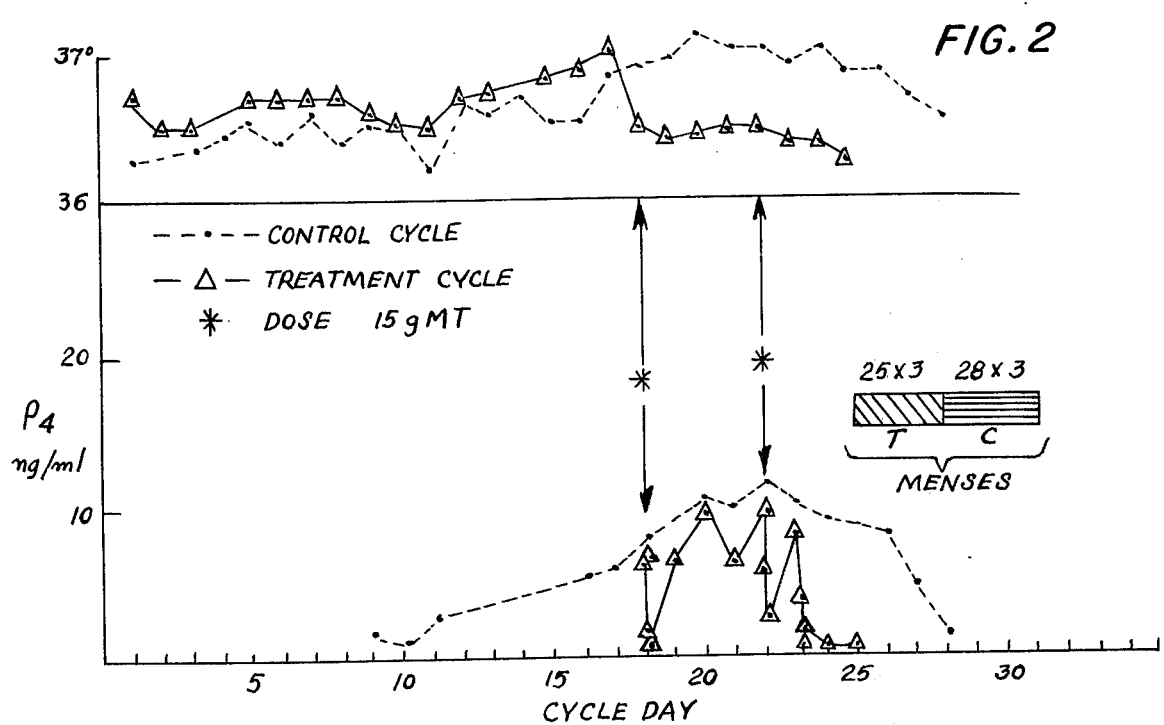

FIG. 2 shows the BBT and ($P_4$) chart during the control cycle and treatment cycle. The MT extract was

| Subject | 1 | 2 | 3 | 4 | 5 | 6 | 7 | 8 | 9 |
|---|---|---|---|---|---|---|---|---|---|
| Age (yrs.) | 36 | 36 | 28 | 29 | 28 | 26 | 35 | 19 | 28 |
| Weight (Kg) | 69.5 | 47.1 | 68.9 | 54.7 | 63.5 | 49.2 | 67.2 | 52.0 | 68.2 |
| Height (meters) | 1.58 | 1.53 | 1.54 | 1.54 | 1.55 | 1.46 | 1.56 | 1.52 | 1.50 |
| Dosage (gMT) | 15 | 15 | 15 | 30 | 30 | 30 | 30 | 30 | 30 |

In each case, MT extract was administered at 8:00 (A.M.) at various days during the second half of the menstrual cycle.

The dosage varied from 15 to 30 gMT and was administered from a single dose up to 9 times. The smallest total amount of MT administered was 30 g., while the largest amount was 270 g. The multiple treatments were administered from 1 to 4 days apart.

Subject No. 1 given the 18th and 22nd days. In this case the treatment cycle was shortened by 3 days and a major decline in the BBT chart was seen 24 hours after the first oral administration of 15 gMT. The only side effects noticed were minor abdominal cramps present on days 19 through 24. Small and transient episodes of sweating lasting 2-3 hours were observed on days 18, 19, and 22, always a few hours after ingestion of the extract. No other side effects were noticed after the adminstration of the extract. The daily plasma levels of progesterone are shown in FIG. 2 and during the control cycle demonstrate the ovulatory patterns. On days 18 and 22 the daily and hourly variation of plasma levels of progesterone were recorded. The plasma levels of progesterone on the 18th day declined from 6.12 ng/ml to 0.64 within three hours. In this subject no major side effects were seen in any of the systems that were monitored.

Subject No. 3

Figure 3:
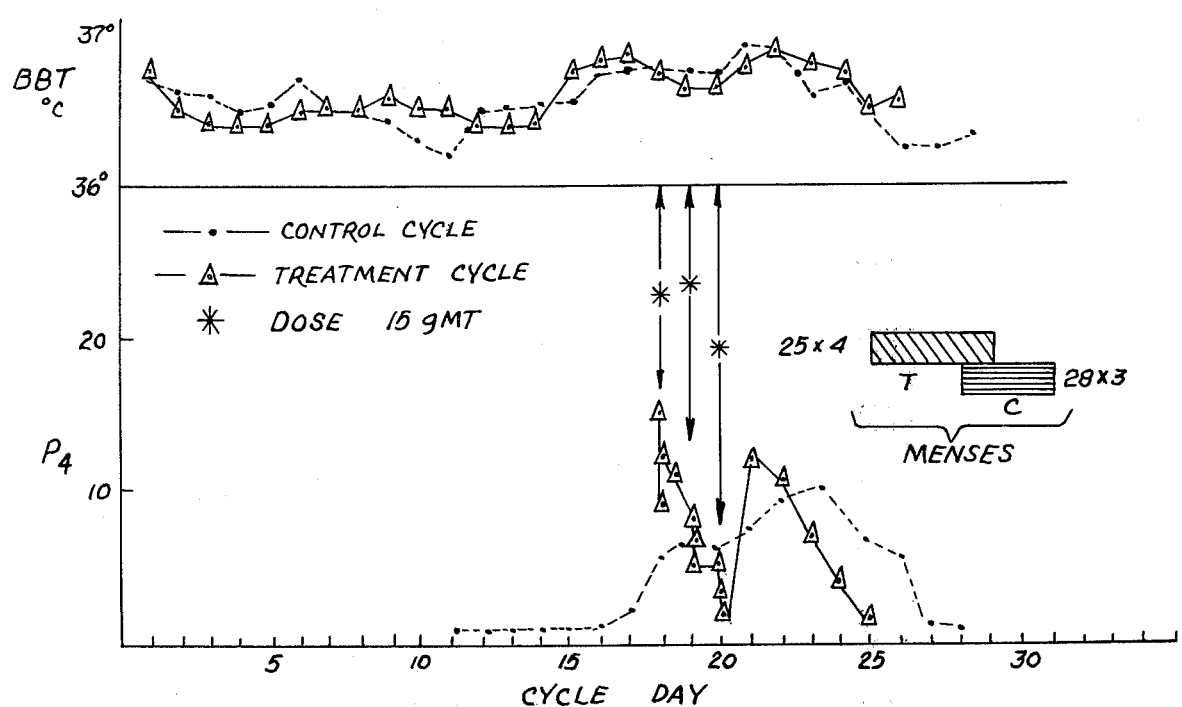

The control cycle in FIG. 3 indicates a normal ovulatory pattern with a length of 28 days and 3 days of menstruation. The MT aqueous extract was given for three consecutive days, starting on day 18 of the cycle. The BBT started to decrease 25 hours after the first dose was administered and continued at somewhat lower levels during the course of the treatment. Sweating was observed on day 18 and mild abdominal cramps appeared from that day until menstruation. On day 18 the basal plasma levels of progesterone were 14.8 ng/ml. The extract was given and the plasma levels of progesterone were reduced to 9.6 within the following 2 hours. In this subject by day 23 the plasma level returned to 11.2 ng/ml, and menses appeared on day 25 with normal characteristics and a duration of 4 days (T=25×4). No major side effects were noticed and all parameters monitored such as blood pressure, respiratory frequency, and gastrointestinal system were normal.

CONCLUSIONS

The treatment of subjects 1–3 permits the conclusion that the MT doses administered have no major side effects; that there was a 3–4 days shortening of the luteal phase; and, that a significant and transient decrease in plasma levels of progesterone was achieved within 3 hours after the oral administration of the MT plant extract.

Subject No. 4

Figure 4:
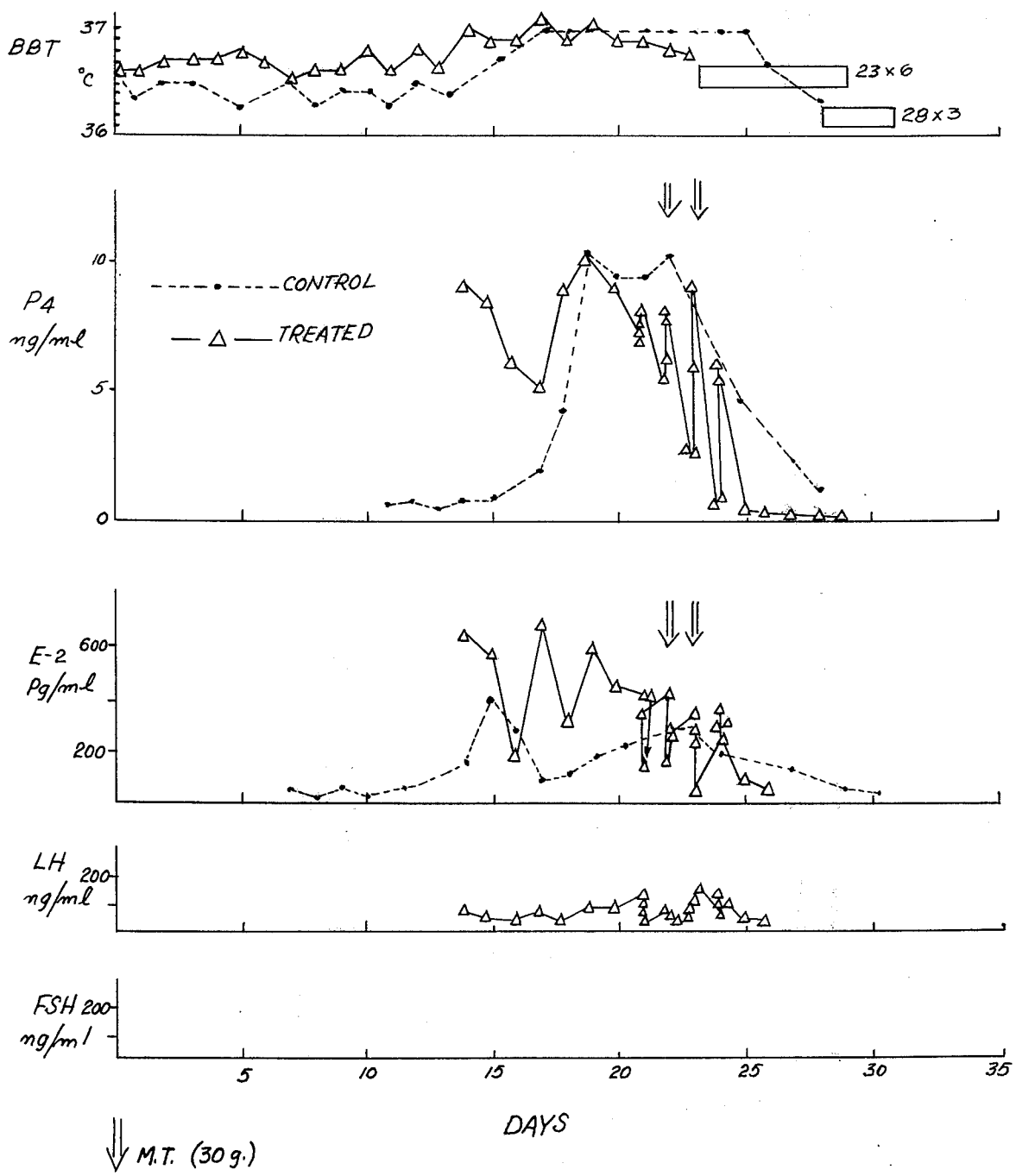

A normal ovulatory pattern is shown in FIG. 4 with a control cycle length of 28 days and 3 days of normal menses (C=28 × 3). In the treatment cycle 30 gMT was administered orally on days 22 and 23. The daily blood plasma levels of 17-$\beta$-estradial ($E_2$) is shown for the control and treatment cycles, expressed in picograms per milliliter (pg/ml). Progesterone ($P_4$), luteinizing hormone (LH) and follicle stimulating hormone (FSH) were estimated along with $E_2$ by radioimmunoassay.

While substantial changes of $P_4$ were not observed on the first two days of the treatment, menses appeared on the 22nd day and lasted for 6 days (T=22=6). $P_4$ levels were reduced considerably by day 24. On day 22, $E_2$ was decreased from 370 pg/ml to 160 pg/ml in less than 1 hour, and 3 hours later was 180 pg/ml. On day 23 the plasma level of $E_2$ had risen to 240 and was decreased to 60 one hour after the second dose of 30 gMT. No major side effects were observed, with only mold abdominal cramps and sweating on the first day of treatment.

Subject No. 5

Figure 5:
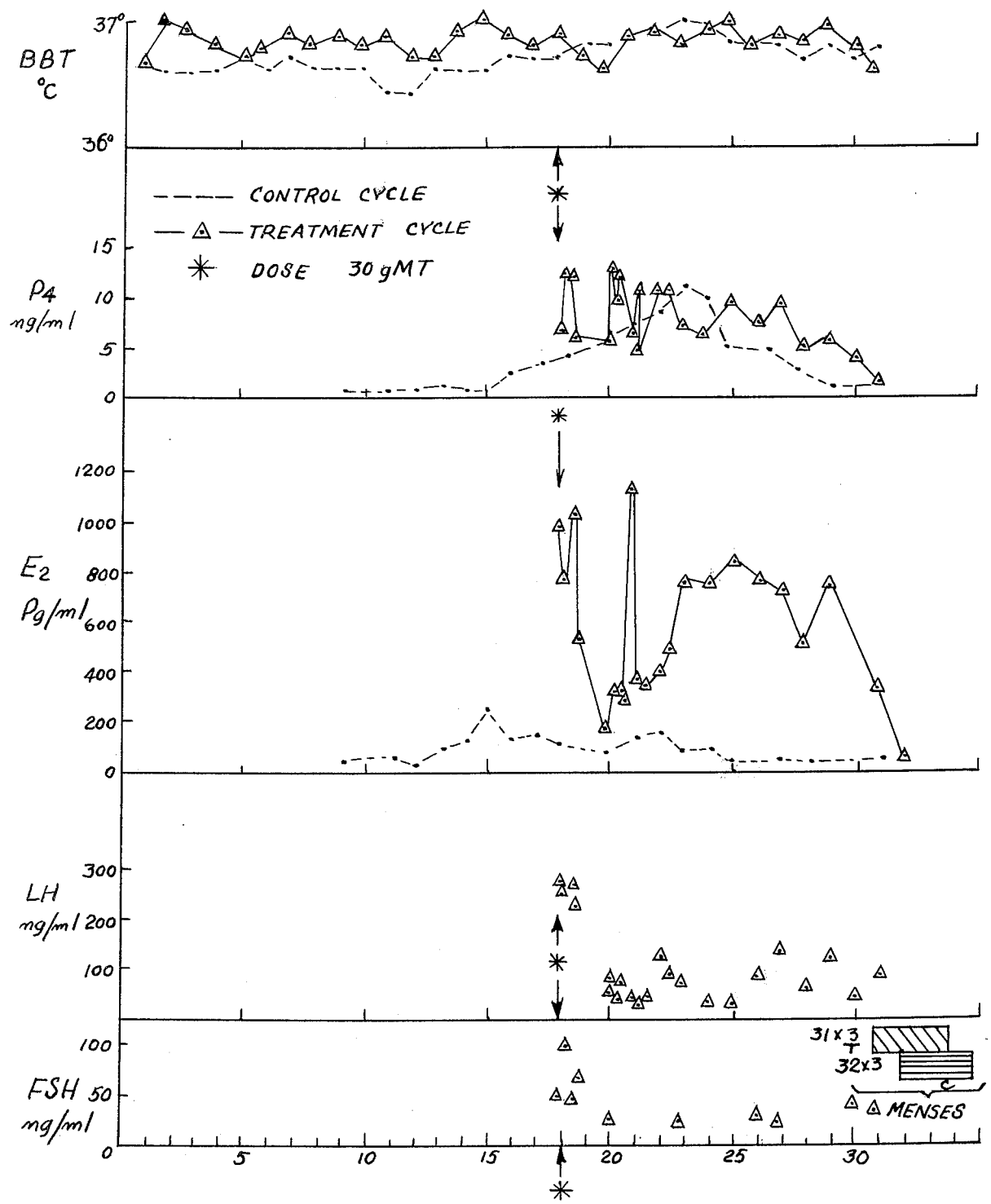

A normal ovulatory pattern is shown in FIG. 5. A single dose of 30 gMT on day 18 of the treatment cycle produced a decrease in body temperature which lasted two days, and heavy intermenstrual bleeding was observed 12 hours after the oral administration of MT extract. The dosage was not repeated. Despite the midcycle bleeding the total cycle length was not reduced and the normal episode appeared on day 32. Minor sweating and abdominal cramps were present 48 hours after the administration; however, there were no changes in the vital functions of cardiovascular, gastrointestinal, renal and respiratory systems. The plasma levels of $P_4$, FSH and LH do not appear to have major changes in this subject; however, basal levels of $E_2$ were reduced from about 1000 pg/ml to 500 pg/ml within three hours after the MT administration.

Subject No. 6

Figure 6:
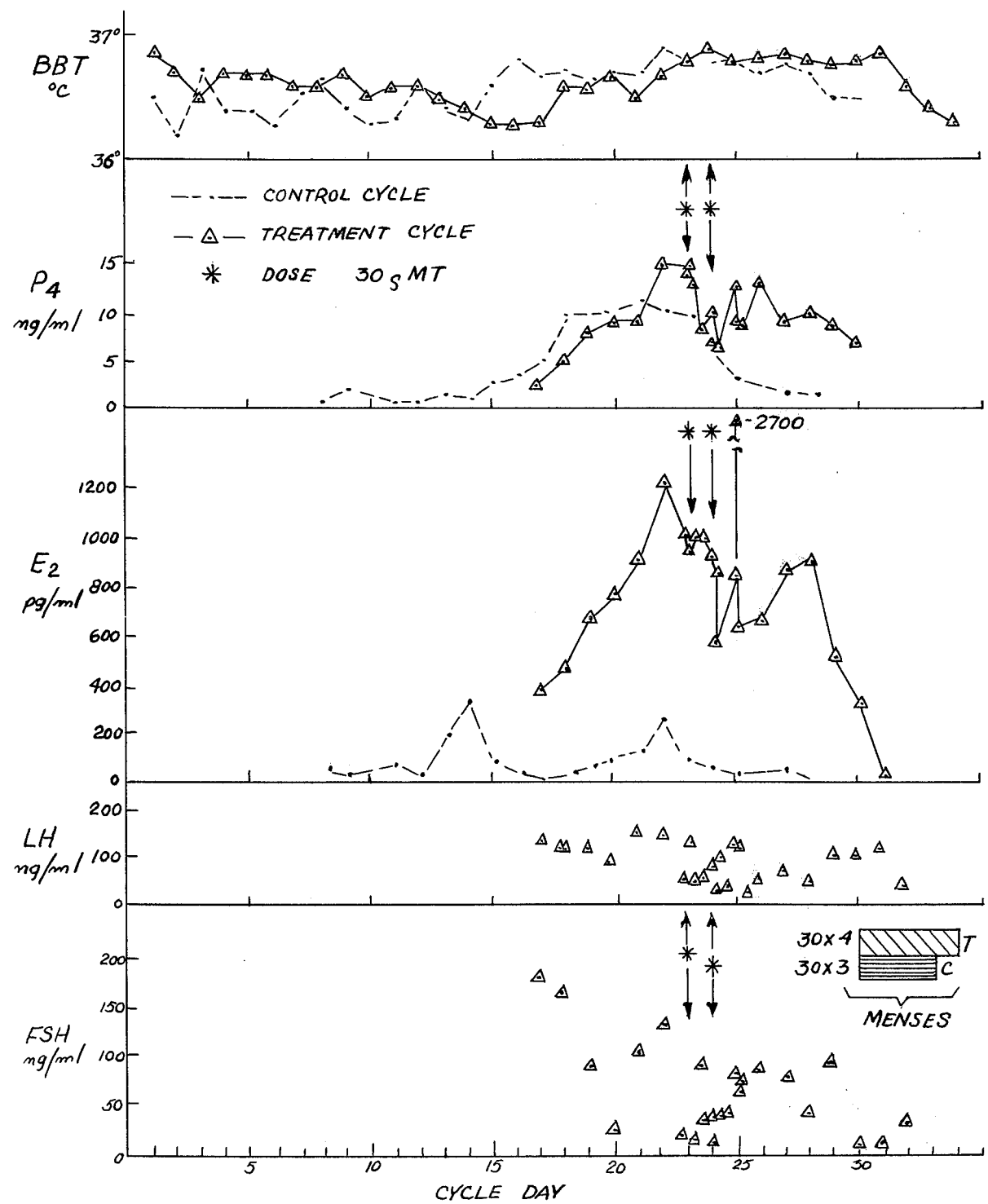

A normal period of 30 days is shown for the control cycle in FIG. 6, indicating a regular ovulatory pattern. Oral administration of 30 gMT was on days 23 and 24 which fall in the luteal phase of the cycle. It is, of course, necessary that the extract be administered during the luteal phase to be effective. Decrease of BBT was observed immediately and heavy intermenstrual bleeding was observed 18 hours after the second dose. After the first 30 g. dose, $P_4$ was lowered from 9.7 ng/ml to 6.8 within three hours, and $E_2$ was lowered from 800 to 500 pg/ml. No major changes in LH or FSH were seen. An extremely high level of estradiol was found on day 25 (2700 pg/ml). The intermenstrual bleeding did not interfere with the appearance of a menses on the 31st day with a duration of 4 days.

As part of the studies on antifertility in primates, *Montanoa tomentosa* was administered to humans and baboons in an induced pseudo-pregnant state or an actual pregnant state. The MT extract was found to reduce blood levels of progesterone in both cases. The luteolytic amount of MT extract for pregnant baboons was about one-fourth that employed for inducing menses in humans; however, it is believed a proportionately larger dose, on a gMT/Kg weight basis, is required to induce menses in the smaller mammals. Substantial transient reductions in $P_4$ are observed in pregnant baboons in the 20th to 51st day of gestation.

Four human females were placed in a state of induced pseudo-pregnancy by administration of human chorionic gonadotropin (HCG, 5000 I.U.) intramuscularly. Three of these (Subjects 7–9) were also treated with MT extract. HCG is known to prolong the menstrual cycle and induce high levels of $P_4$ in humans.

The female subject not treated with zoapatle had a normal ovulatory pattern (C=28×3) prior to administration of HCG. An increased cycle of 37 days including a longer luteal period of 9 days was observed when the subject was given 5000 I.U. doses of HCG, on days 18, 19, and 20 of the pseudo-pregnant cycle.

Subject No. 7

Figure 7:
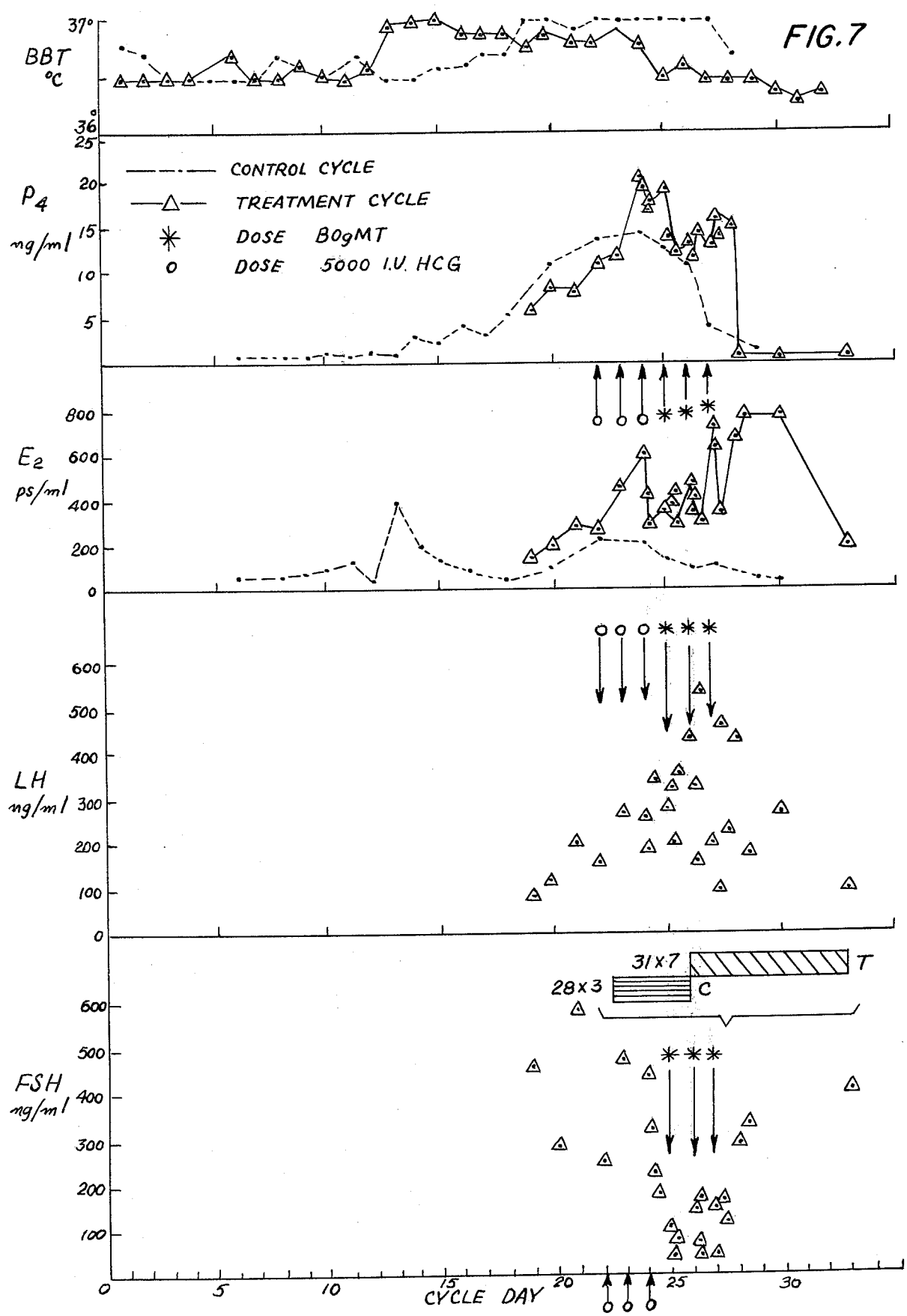

A normal ovulatory pattern is indicated by FIG. 7 during the control cycle (C=28×3). HCG was given in three doses by exogenous administration for three days (22, 23, 24) prior to MT treatment on days 25, 26, and 27. Minor abdominal cramps were observed but, no major side effects were noted. Following the first dose of MT extract, $P_4$ was reduced from 18.7 to 12.6 ng/ml within three hours. No major changes in LH or FSH were found; however, the expected increase in the length of the luteal phase was not observed, since menses began on day 31. Based on the data set out in the paragraph immediately above it could be expected that menses would begin about day 37 rather than day 31.

Subject No. 8

Figure 8:
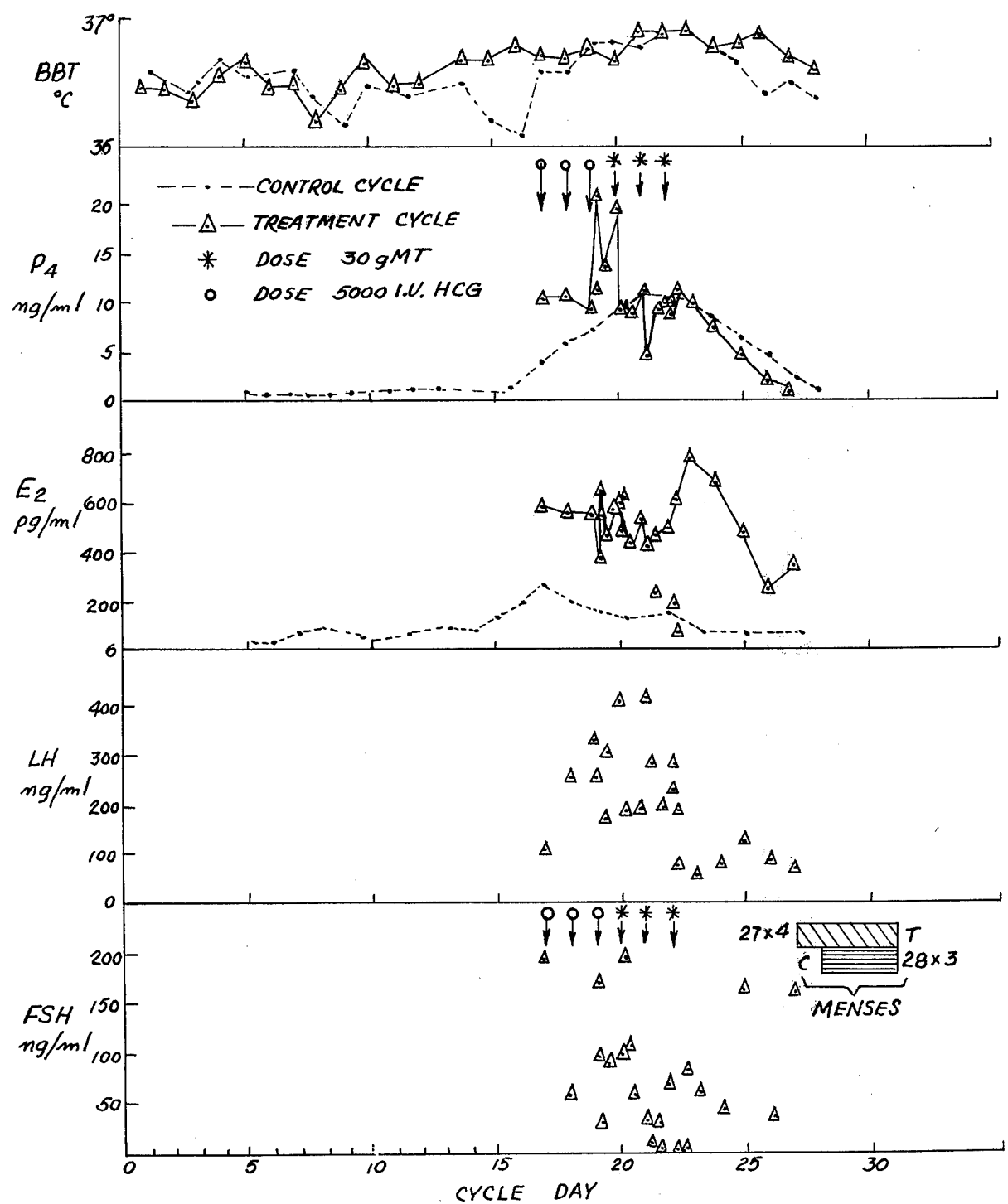

In the normal pattern of the control cycle shown in FIG. 8 a length of 28 days with 3 days of menstrual bleeding was observed. HCG was administered on days 17, 18, and 19, followed by 30 gMT on days 20, 21, and 22. Mild abdominal cramps were observed on day 20 and 21 with small transient sweating on these same days. No major side effects were noted. Despite the HCG stimulations no increase in the cycle is observed (C=28×3, T=27×4). Following the initial dose of 30 gMT, $P_4$ was decreased from 18.3 to 9.4 ng/ml in three hours. Plasma levels of estradiol on day 20 were estimated at 590 mg/ml and within 3 hours after the oral administration of the extract decreased to 518 pg/ml. Next day basal levels of estradiol were 580 pg/ml and within 3 hours came down to 89 pg/ml. The basal levels of estradiol on the 22nd day of the cycle were 469 pg/ml and 3 hours later they were estimated at 97 pg/ml. A similar trend was observed with the hourly estimate of LH of days 20, 21, and 22, after the oral administration of the extract. No major change was observed in FSH levels.

Subject No. 9

A control cycle with normal ovulatory pattern (C=30×3) is shown in FIG. 9.

On days 21, 22, and 23 this subject received 3 consectutive intramuscular doses of 5000 I.U. of HCG, followed by 9 consecutive daily doses of 30 gMT. The decrease in the BBT chart was evident on day 29, after the 6th dose of MT. The expected increase in the length of the menstrual cycle due to induced pseudopregnancy (T=32×3) was not observed. The only side effects observed were minor and transient abdominal cramps present on days 24, 25, and 26 with a small episode of sweating on day 25. Following HCG administration there is a tendency to increase the plasma levels of progesterone on days 21, 22, and 23 as well as an increase of plasma levels of FSH and LH. The MT extract was administered days 24 through 32. Plasma levels of progesterone on day 27, prior to the administration, were 16.7 ng/ml and within 5 hours the plasma levels decreased to 15.2 ng/ml. The next day the basal levels of plasma progesterone were 20.3 ng/ml; the extract was administered and within three hours $P_4$ levels came down to 14.0 ng/ml. From that day the plasma levels of progesterone tended to decrease to 0.2 ng/ml on day 32 when menses appeared. Plasma levels of estradiol on day 27 were 1060 pg/ml and within 3 hours of MT administration decreased to 300 pg/ml. The following days there were no important changes in plasma levels of $E_2$, FSH or LH. Menses was of normal characteristics and normal length. No major side effects were observed. The menstrual cycles preceding and following the treatment cycle were completely normal in length and characteristics of menstruation. While the invention has been described by detailed examples, there is no intent to limit the inventive concept except as set forth in the following claims.

We claim:

1. A composition for reducing progesterone in female mammals which includes a pharmaceutically acceptable carrier and an effective amount of progesterone-regulating substance obtainable by aqueous extract of *Montanoa tomentosa* leaves and stems, said extract being produced by heat and a standard extraction ratio of about 75 grams to 150 grams of *Montanoa tomentosa* per liter of water at about 100° C.

2. The composition of claim 1 wherein the substance is obtained by extraction of about 75 to 150 grams of *Montanoa tomentosa* per liter of boiling water.

3. A composition according to claim 1 wherein said composition is effective in amount to induce menses in primates by progesterone control while having no deleterious side effect.

4. A process for administering the composition of claim 1 wherein the blood plasma progesterone level is regulated to interrupt pregnancy.

5. A unit dosage pharmaceutical composition suitable for inducing menses containing the active menses-inducing component of *Montanoa tomentosa* and a pharmaceutically acceptable carrier for internal use, said active component being obtainable in physiologically compatible form by aqueous extraction of the leaves and stems of *Montanoa tomentosa*, wherein the extraction ratio is about 75 grams to 150 grams of *Montanoa tomentosa* per liter of water with heating at about 100° C and said composition containing an amount of said active component to reduce progesterone in blood plasma.

6. The composition of claim 5 wherein the active component is obtained by extraction of about 75 to 150 grams of *Montanoa tomentosa* per liter of boiling water.

7. In a method for inducing menses in adult female primates by internal administration of an effective amount of a menses-inducing composition in pharmaceutically acceptable form, the improvement wherein the menses-inducing composition consists essentially of a luteolytic amount of the active product from the leaves and stems of *Montanoa tomentosa* which is soluble in water with heating at about 100° C, and the extraction ratio is about 75 grams to 150 grams of *Montanoa tomentosa* per liter of water.

8. The method of claim 7 wherin the composition is administered to a pregnant female in sufficient amounts to terminate pregnancy.

9. A method for synchronizing the estrous cycle in a group of mammals which consists essentially of (a) preventing conception by administering to each member of the group internally a progesterone-regulating amount of *Montanoa tomentosa* active product obtainable by extraction of 75 grams to 150 gram of leaves and stems per litter of water with heat at about 100° C; (b) subsequently permitting members of the group to become fertile in a close time period; and (c) delivering newborn animals at term or near term in a biologically synchronized time span.

10. The method of claim 9 wherein the active product is obtained in quantities equivalent to extraction of about 75 to 150 grams of *Montanoa tomentosa* per liter of boiling water.

11. The method of claim 9 wherein the group of mammals is a flock of sheep.

12. The method of claim 9 wherein the group consists of cattle.

13. A method of preventing births in female mammals comprising
orally administering post-coitally to a female mammal a non-toxic, effective antifertility dosage of Montanoa tomentosa extract, said extract being obtainable by boiling 75 grams to 150 grams of leaves and stems of the plant per liter of water at about 100° C.

14. The method of claim 13 wherein the dosage is equivalent to about ¼ to 40 gMT/Kg of body weight.

15. The method of claim 14 wherin at least two daily doses are administered.

16. The method of claim 15 wherein the doses are administered during the luteal phase of a menstrual cycle.

17. An internally administered pharmaceutical composition for controlling blood levels of progesterone which consists essentially of a luteolytic amount of *Montanoa tomentosa* extract, said extract having been prepared from 75 grams to 150 grams of the stems and leaves per liter of water at about 100° C and contained in a pharmaceutically acceptable carrier.

* * * * *